(12) United States Patent
Kronenthal

(10) Patent No.: US 8,603,528 B2
(45) Date of Patent: *Dec. 10, 2013

(54) COMPOSITIONS AND METHOD FOR THE REDUCTION OF POST-OPERATIVE PAIN

(75) Inventor: Richard L. Kronenthal, Fairlawn, NJ (US)

(73) Assignee: ABYRX, Inc., Irvington, NY (US)

( * ) Notice: Subject to any disclaimer, the term of this patent is extended or adjusted under 35 U.S.C. 154(b) by 1988 days.

This patent is subject to a terminal disclaimer.

(21) Appl. No.: 11/492,083

(22) Filed: Jul. 25, 2006

(65) Prior Publication Data

US 2006/0280801 A1 Dec. 14, 2006

Related U.S. Application Data

(63) Continuation-in-part of application No. 10/941,890, filed on Sep. 16, 2004.

(60) Provisional application No. 60/702,226, filed on Jul. 25, 2005, provisional application No. 60/758,300, filed on Jan. 12, 2006.

(51) Int. Cl.
*A61F 2/00* (2006.01)
*A61K 9/14* (2006.01)

(52) U.S. Cl.
USPC .......................... 424/484; 424/426; 424/489

(58) Field of Classification Search
None
See application file for complete search history.

(56) References Cited

U.S. PATENT DOCUMENTS

| | | |
|---|---|---|
| 2,611,706 A | 9/1952 | Bernhart et al. |
| 2,770,569 A * | 11/1956 | Fromherz et al. ............. 514/282 |
| 3,924,000 A | 12/1975 | Thiele |
| 4,186,448 A | 2/1980 | Brekke |
| 4,439,420 A | 3/1984 | Mattei et al. |
| 4,443,430 A | 4/1984 | Mattei et al. |
| 4,568,536 A | 2/1986 | Kronenthal |
| 4,588,583 A | 5/1986 | Pietsch et al. |
| 4,650,665 A | 3/1987 | Kronenthal |
| 4,770,803 A | 9/1988 | Forsberg |
| 5,047,166 A | 9/1991 | Weil |
| 5,073,373 A | 12/1991 | O'Leary et al. |
| 5,143,730 A | 9/1992 | Fues et al. |
| 5,284,655 A | 2/1994 | Bogdansky et al. |
| 5,290,558 A | 3/1994 | O'Leary et al. |
| 5,314,476 A | 5/1994 | Prewett et al. |
| 5,356,629 A * | 10/1994 | Sander et al. ................. 424/422 |
| 5,454,787 A | 10/1995 | Lundquist |
| 5,484,601 A | 1/1996 | O'Leary et al. |
| 5,496,819 A | 3/1996 | Okuyama et al. |
| 5,595,735 A * | 1/1997 | Saferstein et al. ......... 424/94.64 |
| 5,641,502 A | 6/1997 | Skalla et al. |
| 5,681,873 A | 10/1997 | Norton et al. |
| 5,696,101 A | 12/1997 | Wu et al. |
| 6,030,635 A | 2/2000 | Gertzman et al. |
| 6,117,444 A | 9/2000 | Orgill et al. |
| 6,139,872 A * | 10/2000 | Walsh ........................... 424/464 |
| 6,174,422 B1 | 1/2001 | Honig et al. |
| 6,264,973 B1 * | 7/2001 | Mahashabde et al. ........ 424/432 |
| 6,328,979 B1 * | 12/2001 | Yamashita et al. ............ 424/400 |
| 6,331,313 B1 | 12/2001 | Wong et al. |
| 6,355,705 B1 * | 3/2002 | Bond et al. .................... 523/118 |
| 6,413,539 B1 | 7/2002 | Shalaby |
| 6,420,454 B1 | 7/2002 | Wenz et al. |
| 6,437,018 B1 | 8/2002 | Gertzman et al. |
| 6,454,787 B1 | 9/2002 | Maddalo et al. |
| 6,485,749 B1 | 11/2002 | Shalaby |
| 6,565,884 B2 | 5/2003 | Nimni |
| 6,576,249 B1 | 6/2003 | Gendler et al. |
| 6,960,346 B2 | 11/2005 | Shukla et al. |
| 2002/0090398 A1 | 7/2002 | Dunn et al. |
| 2003/0049326 A1 | 3/2003 | Nimni |
| 2003/0093157 A1 | 5/2003 | Casares et al. |
| 2004/0018238 A1 | 1/2004 | Shukla et al. |
| 2004/0109893 A1 | 6/2004 | Chen et al. |

(Continued)

FOREIGN PATENT DOCUMENTS

| | | |
|---|---|---|
| EP | 0537559 | 4/1993 |
| GB | 1584080 | 2/1981 |

(Continued)

OTHER PUBLICATIONS

New Zealand Examination Report, Application No. NZ 563557, Date: Nov. 13, 2009.
Chinese Office Action, Application No. CN 200480027547.5, Date: Sep. 25, 2009.
Supplementary European Search Report, Application No. EP04781435.5, Mail Date: Jul. 17, 2009.
International Preliminary Report, Application No. PCT/US2004/026738, Date of Issuance: Apr. 3, 2007.
International Preliminary Report, Application No. PCT/US2006/028823, Date of Issuance: Jan. 29, 2008.
Examiner'S First Report on Patent Application No. 2006272663 (AU), Dated: Jul. 8, 2009; Date Received: Aug. 11, 2009.
Examination Report, Application No. EP 04781435.5, Date: Nov. 24, 2009.

(Continued)

*Primary Examiner* — Juliet C Switzer
*Assistant Examiner* — Caralynne Helm
(74) *Attorney, Agent, or Firm* — Mintz Levin Cohn Ferris Glovsky and Popeo, P.C.; Ivor E. Elrifi; Muriel Liberto, Esq.

(57) ABSTRACT

At least three component, body-implantable, absorbable, biocompatible, putty, and non-putty pain-relieving compositions for use in surgery comprising in intimate admixture: an analgesic having local pain-relieving activity for internal relief of pain, a finely powdered bulking material, preferably less than 50 microns, e.g. the metal salts of fatty acid, hydroxyapatite, DBM, polyglycolide, polylactide, polycaprolactones, absorbable glasses, gelatin, collagens, mono, and polysaccharides starches.
An organic liquid capable of solubilizing, dispensing or suspending the analgesic, such as esters of monohydric alcohols with aliphatic monocarboxylic acids; $C_2$-$C_{18}$ monohydric alcohols with polycarboxylic acids; $C_8$-$C_{30}$ monohydric alcohols; tocopherol and esters thereof with mono or polycarboxylic acids; free carboxylic acids such as oleic, capric, and lauric; dialkyl ethers and ketones; polyhydroxy compounds and esters and ethers thereof; random or block copolymers of ethylene oxide and propylene oxide.

18 Claims, No Drawings

(56) References Cited

U.S. PATENT DOCUMENTS

| | | |
|---|---|---|
| 2005/0065214 A1 | 3/2005 | Kronental |
| 2005/0113341 A1 | 5/2005 | Timmer et al. |
| 2005/0153869 A1 | 7/2005 | Connor et al. |
| 2006/0002976 A1 | 1/2006 | Kronenthal |
| 2006/0013857 A1 | 1/2006 | Kronenthal |

FOREIGN PATENT DOCUMENTS

| | | |
|---|---|---|
| WO | WO 95/22360 | 8/1995 |
| WO | WO 96/39995 | 12/1996 |
| WO | 00/45867 A1 | 8/2000 |
| WO | WO 0176649 A1 * | 10/2001 |
| WO | 2005/034726 A2 | 4/2005 |
| WO | 2007/014210 A2 | 2/2007 |
| WO | 2005/034726 A3 | 5/2007 |
| WO | 2007/014210 A3 | 10/2007 |

OTHER PUBLICATIONS

Jain et al., "Vitamin E and the hypercoagulability of neonatal blood," Clinica Chimica Acta 225:97-103 (1994).

Murohara, T., et al., Inhibition of platelet adherence to mononuclear cells by α-Tocopherol of P-Selectin. Circulation 141-148 (2004).

Steiner, M. et al., Vitamin E: An inhibitor of the platelet release reaction. J. Clin. Inv. 57:732-737 (1976).

* cited by examiner

US 8,603,528 B2

COMPOSITIONS AND METHOD FOR THE REDUCTION OF POST-OPERATIVE PAIN

CROSS REFERENCE TO RELATED APPLICATIONS

This application claims the benefit of U.S. Provisional Application 60/504,978, filed Sep. 23, 2003, Provisional Application No. 60/702,226 filed Jul. 25, 2005, Provisional Application No. 60/758,300 filed Jan. 12, 2006 and U.S. patent application Ser. No. 10/941,890 filed Sep. 16, 2004 all of which are incorporated herein by reference as though they were set forth verbatim herein This application is a Continuation-In-Part of U.S. Ser. No. 10/941,890 filed Sep. 16, 2004 entitled "Absorbable Implants and Methods For Their Use In Hemostasis and In The Treatment of Osseous Defects"

STATEMENT REGARDING FEDERALLY SPONSORED RESEARCH OR DEVELOPMENT (Not Applicable)

REFERENCE TO A SEQUENCE LISTING, A TABLE, OR A COMPUTER PROGRAM LISTING APPENDIX SUBMITTED ON COMPACT DISC (SEE 37 CFR 1.52(e)(5))

(Not Applicable)

BACKGROUND OF THE INVENTION

Field of Invention

This invention relates to the surgical delivery of body implantable compositions comprising one or more anesthetics or analgesics having local pain-relieving activity, for the management of postoperative pain. The terms "analgesics" and "anesthetics" are used interchangeably herein.

The relief of postoperative pain is an important aspect of surgical pain management. Systemic drugs such as NSAIDs, opioids and other analgesics or anesthetics are known to have significant clinical drawbacks. Other methods toward this end, such as external pumps that infuse aqueous solutions of local anesthetics through percutaneous transdermal catheters into the area of the surgical wounds, have been employed, but have not been considered totally acceptable.

During and following surgical procedures, soluble local anesthetics in the form of aqueous solutions, often are infused into or around the operative site to reduce pain associated with operative trauma. Unfortunately, they are relatively short-lived in their action.

Water solubility is made possible because most local anesthetics are basic as a result of the presence of an amino moiety and they readily form water-soluble salts with acids. Anesthetics in the free base form, however, usually are essentially water-insoluble and, in this form, are not deliverable using conventional aqueous systems. An exception involving the use of the free base involves topical anesthesia where the anesthetic base is dissolved in a non-aqueous ointment carrier, e.g., petroleum jelly, and, as such, applied to the surface of the skin.

The duration of action of a local anesthetic is proportional to the time during which it is in actual contact with neural tissue. Local anesthetics reversibly block impulse conduction in neural tissue thereby producing a transient loss of sensation in a circumscribed area of the body. Thus, local anesthetics may be used to prevent pain during surgical procedures. To prolong the action of local anesthetics, vasoconstrictor drugs such as norepinephrine, often are added to the anesthetic solution. Generally speaking, duration of pain relief much after the termination of the surgical procedure is not usually obtained.

Local anesthetics may be divided into two groups, depending upon their solubility in water: the slightly soluble compounds and the soluble compounds. The slightly soluble compounds are used only for topical anesthesia and are of relatively longer duration. On the other hand, only the soluble anesthetics can be used for infiltration anesthesia. Local anesthetics may be further classified according to their chemical structures, e.g., those having moieties joined through ester or amide linkages. In general, the esters are more toxic and short-lived while the amide type anesthetics have a longer duration of action.

A difficulty with one prior art approach to post-operative pain relief is that the infused analgesic generally does not remain at the operative site for a suitable period of time. The present invention is directed to that aspect of the prior art approach. That is, the invention intends to provide an implantable, slowly absorbable composition which releases analgesic material into the operative site, post-operatively.

In the present inventor's U.S. patent application Ser. No. 10/941,890, filed Sep. 16, 2004, now United States Patent Publication No. 2005-0065214-A1, Published Mar. 24, 2005 (incorporated herein by reference for all purposes), absorbable systems such as putty-like and non-putty like substances are described and claimed for the treatment of osseous defects and the control of bleeding from cut or traumatized bone and soft tissue. An important characteristic of many of the described systems is that they are anhydrous and have an organic component in which free bases of local anesthetics are soluble.

The '890 application priority claimed herein; discloses the incorporation of analgesic drugs into the vehicle to mediate pain. Conventionally, the acid addition salt, the hydrochloride, for example, of a local anesthetic, would be admixed with an appropriate vehicle, a putty, for example. It was thought that the water-soluble hydrochloride would be eluted from the vehicle relatively rapidly (as compared to the slightly soluble free base) in the aqueous environment of the body and longer term effectiveness would be reduced.

In Provisional Application Ser. No. 60/758,300, filed Jan. 12, 2006, priority of which is claimed herein, the inventor herein disclosed that the combination of an organic-soluble free base and a water-soluble hydrochloride (or other acid addition salt) of the same or different anesthetic agent, would form a surgically implantable, absorbable combination providing extended pain management wherein the water-soluble component would elute relatively rapidly for early pain relief and the water-insoluble free base component would elute more slowly for extended pain relief. The basic concept of the invention was to combine the water-soluble salt, e.g., hydrochloride, of an anesthetic together with its corresponding free base (or the free base form of another analgesic) in a substantially anhydrous, non-aqueous composition and then implant the composition for pain relief. The hydrochloride portion of the anesthetic e.g., lidocaine hydrochloride, was thought to be elutable from the system relatively rapidly while the free base, e.g., lidocaine, dissolved in the non-aqueous carrier, would elute more slowly to extend the effectiveness of pain mediation. Because the carrier composition is absorbable in the body, any insoluble free base residue will be exhausted from the implant site as the implant is absorbed. Thus, extended anesthetic efficacy, not heretofore possible using aqueous media, was thought to be easily achieved.

BRIEF SUMMARY OF THE INVENTION

It has now been found, in accordance with the present invention, that an analgesic agent having the capability of providing intraoperative pain relief at an internal surgical site may be provided from an implant composition comprising a solid material in finely powdered form, intimately admixed with an organic liquid and an anesthetic agent to be described in more detail below. The composition is an absorbable, anhydrous or essentially anhydrous implant which imparts post-surgical pain relief over suitable period of time when an appropriate non-aqueous liquid dispersing vehicle and an anesthetic having local pain-relieving activity is included therein.

Thus, the elements of the anhydrous or essentially anhydrous composition of the invention may be said to comprise the following three main categories in intimate admixture:
  Component 1. a body-implantable, biocompatible, finely divided solid material.
  Component 2. an organic liquid, capable of dispersing or suspending Component A.
  Component A. an anesthetic compound, or mixture of compounds, having local pain-relieving activity.
  Component B. an optional elution control agent which may be added to aid in controlling the rate of release of the anesthetic from the the implant.

If the end compound is desired to be anhydrous, then each of the components should be anhydrous. If the final composition is to be essentially anhydrous, then each component may itself be water-carrying. Anhydrous components may be used with additional water optionally being added after or at any time during the blending of the components.

The components, when blended together, yield either the anhydrous composition or the essentially anhydrous composition of the invention, depending upon the nature and ratios of the components, resulting in a variety of physical forms such as putties, lotions, gels, creams and the like depending on the quantity of liquid Component 2. The composition is preferably sterile.

The compositions of the invention provide an elutable source of analgesic when implanted at an internal surgical site. Active analgesic is generally elutable over a period of from about 0 to 8 days, post-surgery, during which time a pain-relieving effective amount is released.

An important characteristic of the composition which affects the release rate of the analgesic is the consistency or viscosity of the composition. In general, lower viscosity compositions tend to release the product more rapidly than higher viscosity compositions. The viscosities may range at the lower end from the freely flowable liquids, such as lotions and other liquids which quickly take the shape of the container boundaries, if left unimpeded, and which would flow out of the container by gravity if allowed to, to the higher viscosities of slowly flowable liquids such as those having the viscosity of thick shampoos, honey, molasses and the like, to semi-solid materials such as gels, pastes, and creams, which are generally non-flowing under ambient conditions, to the moldable materials such as putties, waxes and other such materials which tend to remain in place when applied to a site, up to the hard, solid materials which are not moldable under ambient conditions, such as preformed, shaped materials such as rods, buttons and the like.

Adjustment of the type and amount of Component 2 will also have an effect on elution of the analgesic from the final product. For example, hydrophobic materials such as the tocopherols, tocopheryl acetate, for example, tend to slow down the elution rate.

Different anesthetics can be expected to yield different elution rates, as well, especially if they are present in particulate form. Thus, suspendable or dispersible anesthetics should be in finely divided form having relatively uniform particle size distribution, to lend a more reliable elution rate profile than would be obtained with larger or polydispersed particles.

The preferred manner of producing the composition is to dissolve, disperse or suspend the anesthetic compound in the liquid Component 2, optionally admixed with an elution control agent, to form a solution, dispersion or suspension, which is then mixed with the solid phase Component 1 to form a blend of all components. The physical form of the said product, i.e. putty, gel, lotion, or the like, depends upon the physical characteristics and relative quantity of the components. The most preferred form for surgical procedures is the so-called putty form. The invention in its preferred form, thus provides a body-implantable, biocompatible, essentially anhydrous, sterile, body-absorbable composition comprising Components 1, 2 and A, optional Component B and any other optional components, to be described below, which are left to the discretion of the user and the particular application sought.

Once implanted into the body of a surgical patient, the entrapped anesthetic will diffuse from the implant into surrounding tissue where pain signals to the brain from traumatized local nerve endings are interrupted. The compositions may contain either the slightly water-soluble anesthetics in acid addition salt form or in the free base form, or both, to provide flexibility and variation in the availability of pain relief depending on the circumstances. In such cases, the salt is previously dispersed throughout Component 1 or alternatively dispersed in Component 2, and the dispersion thereafter intimately admixed with the solid phase Component 1 to form a dispersion. If a free base soluble in the organic medium is also used, it remains solubilized in the organic medium which is blended with the solid phase and is eluted along with the salt, albeit not at the same rate.

It has further been found, in accordance with the invention, that the ingredients of the implantable composition may be varied in concentration to provide differing drug elution rates. For example, in a putty-like composition comprising lidocaine free base, calcium stearate and liquid triethyl citrate, the free base of lidocaine is released over a three day period. If the liquid component of the putty is changed from triethyl citrate to Pluronic® L-35 (a liquid block copolymer of ethylene oxide and propylene oxide) and tocopheryl acetate, the free base of lidocaine is eluted over an eight day period. Mixtures of liquid Pluronics® and solid Pluronics® will extend the elution time over that of liquid Pluronic® alone. Our studies indicate that tocopheryl acetate reduces the elution rate while tricalcium phosphate, and hydroxyapatite increase the elution rate. The free base elutes faster than the acid addition salt, and in a free base/salt mixture the free base surprisingly elutes more rapidly. Other non-toxic, non-aqueous liquid components, for example, ethers (such as polyalkylene glycols) in which the anesthetic free base is miscible, may be similarly employed.

The formulations of the present invention are compositions having various viscosities and cohesive strengths and include putty and non-putty formulation consistencies. The term "putty" is used herein as it is used in the art and is generally known to the skilled artisan. Dough (such as pastry dough), modeling clay, and glazier's putty of varying viscosities, depending on the indications and ultimate use, are examples of the consistency of a suitable product. Putties of various viscosities useable in the invention include those that are capable of adhering to bone. In general, putties which are soft, moldable, preferably non-elastic, cohesive mixtures prepared from a finely powdered substance (Component 1) intimately admixed with the organic liquid (Component 2) and having a shape which is capable of being deformed in any direction, are suitable consistencies for the putty-like compositions of the invention. As described herein, however, compositions which have lower cohesive strengths than the putties described above, are within the scope of the invention, and may be used in specific applications in which the more viscous, higher cohesive strength putties are less suitable.

For purposes of this invention, a major difference between putties of the invention and materials not considered to be putties (herein non-putties), but which are still within the scope of the invention, is that the non-putties have lower cohesive strengths than the cohesive strengths of the putty formulations and in some cases, may have even higher cohesive strengths than the putties. Individual non-putties of the invention at the lower end of the cohesive strengths range, are characterized by having the cohesive strength of creams, pastes, ointments, lotions, foams, gels, and the like. Their use as implants may be facilitated by providing a lattice or structure to which the non-putties may be applied and the entire structure applied to the operative site. Preferably, the non-putties have only a fraction of the cohesive strength of putties of the invention, tending to be easily collapsible or easily torn apart under small stresses that would not, generally speaking, have the same effect on putties. At the higher end, i.e. at viscosities higher than the putties, the composition can be in the more rigid, formed, non-deformable stage as their ultimate use requires. The description which follows is given mainly in the context of the putties of the invention, it being understood, however, that if other less cohesive strength materials are desired, the skilled artisan will simply make the appropriate changes in the proportions of components or add other substances to achieve the same purpose.

The present invention involves formation of medically useful absorbable putty-like and non-putty-like compositions using virtually any solid phase which is bio-compatible and finely dividable to produce the requisite consistency when blended with the Component 2 liquid carrier.

Many compositions of the invention, in addition to their pain management aspect, are also sterile, absorbable, bone hemostatic agents. That is, they will provide virtually immediate surgical hemostasis, will absorb in the body after a relatively short period of time without compromising hemostasis efficacy and will allow the diffusing of the analgesic to the surrounding operative sites. They would minimally inhibit osteogenesis and subsequent bone healing. They thus would have significant medical advantages over presently available materials. Moreover, bone-healing adjuvants such as growth factors, particularly, for example, platelet derived growth factor (PDGF) and/or bone morphogenic proteins (BMPs) and others, could be added to the formulations to stimulate the bone healing process. Furthermore, adding agents such as collagen, demineralized bone matrix (DBM), and/or hydroxyapatite could make the hemostatic/pain management material beneficially osteoconductive or osteoinductive. The addition of a suitable anti-infective agent such as antibiotics typified by tobramycin and gentamicin or bacteriostatic and bacteriocidal materials such as iodine, silver salts, triclosan, colloidal silver, or the like serve to reduce the potential for infection, particularly in contaminated open wounds such as compound fractures. The addition of colorants would aid in visibility during the operative procedure. The addition of radiopaque substances allows the observation of post-operative sequelae using radiography. The addition of chemotherapeutic agents or radionuclides is useful when the putty is used, for example, in bone cavities arising from tumor resection. While the analgesic compounds to reduce pain, constitute Component A of the composition, vasoconstrictors and/or blood clot-inducing agents to reduce hemorrhage, are useful additives.

DETAILED DESCRIPTION OF THE INVENTION

The compositions of the present invention include compositions comprising at least three, but also possibly four, or more components, at least one of which is an analgesic having local, pain-relieving activity, or combination of such analgesics. They are most preferably body absorbable and biocompatible. In many embodiments they have a putty-like consistency. In one embodiment, the compositions are mechanically hemostatic tamponades useful in stopping the bleeding of bone by the application of the putty-like composition to the affected area while still possessing the ability to release analgesics. By "mechanically hemostatic tamponades" is meant that the compositions function by mechanically compressing the bleeding areas of the bone to arrest hemorrhaging as opposed to functioning by chemically hemostatic means, i.e. the arresting of hemorrhaging, in whole or in part, using a chemical means or agent. Of the at least three components mentioned in the first sentence of this paragraph, Component 1 is a finely powdered carrier vehicle or bulking material having an average particle size sufficiently small to form the desired consistency when intimately admixed with the second component, i.e. an organic liquid Component 2 of the invention in which an analgesic is dissolved, dispersed or suspended.

Illustrations of Component 1 are hydroxyapatite, (as used herein, hydroxyapatite is generic for all forms of calcium phosphate including tricalcium phosphate), a carboxylic acid salt, preferably a fatty acid salt such as calcium stearate or a homolog thereof such as calcium laurate, or other finely powdered agents such as synthetic absorbable polymers, e.g. polyglycolide, polylactide, co-polymers of lactide and glycolide, polydioxanone, polycaprolactone, as well as absorbable glasses, (such as those based upon phosphorus pentoxide and the like). The particular Component 1 solid phase is not particularly limited, and may be virtually any solid which is biocompatible and divisible into fine powder so that compositions of proper consistencies may be formed. Of course, Component 1 is not soluble in Component 2.

The Component 2 dispersing vehicle is an organic liquid which, when intimately admixed with the analgesic Component A and then with Component 1, enables the formation of the putty-like or non-putty-like implant.

While the three-component compositions of the invention provide the basic characteristics of suitable pain-relieving materials, some of which may be hemostatic, as described herein, they may also, if desired, but are not required to, contain optional ingredients illustrated by those shown below. For example, optional Component 3 is an absorption accelerator, and optional Component 4 is a bone growth-inducing material. Other components may be added to provide additional attributes to the putty-like and non-putty like compositions of the present invention as will be explained in more detail below.

Following is a detailed description of the various components.

Component 1

Component 1 is comprised of a finely powdered, preferably micronized, essentially water-insoluble, preferably anhydrous (except for absorbed water), biocompatible, body-absorbable substance which, when admixed with the organic liquid, analgesic-containing Component 2, forms compositions of the invention. Suitable compositions are obtained when the average particle sizes of Component 1 materials are about 100 microns or less, but the preferred average particle size range is between about 3 to about 50 microns and most preferably about 6 to about 25 microns especially when putty-like compositions are desired. Particle sizes for non-putty compositions may range higher than those of the putty compositions, if desired.

Examples of one set of materials suitable for use herein are salts of one or more carboxylic acids having a carboxylate anion and a metal cation, some which are known in the art, having been described in U.S. Pat. Nos. 4,439,420 and 4,568, 536. Suitably, the salts may be the calcium, magnesium, zinc, aluminum, lithium or barium salts of saturated or unsaturated carboxylic acids containing about 6 to 22 carbon atoms in the chain and preferably 8 to 20 carbon atoms. The preferred saturated carboxylic acids supplying the carboxylate anion may be selected from aliphatic acids such as caprylic acid, capric acid, lauric acid, myristic acid, palmitic acid, stearic acid, arachidic acid, and intervening homologs thereof, but the most preferred acids are the higher fatty acids such as lauric, myristic, palmitic, and stearic acids, with stearic being most preferred. Calcium and aluminum palmitates and stearates are preferred salts with calcium stearate being most preferred because of its excellent safety profile, and putty-forming characteristics. However, aluminum stearate, aluminum palmitate, or aluminum laurate, are suitable as well.

Examples of suitable unsaturated aliphatic acids which may be used for supplying the carboxylate cation are oleic acid and linoleic acid for which the same cations described above are used.

It has been discovered that finely divided materials, for example, average particle size of microns about 100, but preferably below 50 microns or less, other than carboxylate salts, can be effective Component 1 substances. For example, it was surprising to find that finely powdered hydroxyapatite, especially when less than about 25 microns in average particle size, formed an excellent putty, especially with tocopheryl acetate or triethyl citrate as the liquid dispersing agent (Component 2).

Furthermore, other materials, some of which are discussed in connection with Component 4, are useful as Component 1 when provided in finely powdered form. Examples of these are demineralized bone matrix (DBM), mineralized bone matrix (MBM), insoluble absorbable collagens, gelatin derived from collagens, monosaccharides, and polysaccharides. It is thought that any biocompatible material, when converted to very small particle sizes, will form medically useful compositions for use in the present invention. It would not be uncommon, when producing compositions of the present invention, to have, for example, hydroxyapatite (or any calcium phosphate or tricalcium phosphate) particles of around 20-30 microns as Component 1, a suitable Component 2, as described below, a suitable Component A, and bone chips such as a demineralized bone matrix or a mineralized bone matrix having a particle size of about 0.5 to about 1 mm or larger as Component 4.

Other examples of Component 1 substances are finely milled synthetic absorbable homo- and co-polymers, e.g., polyglycolide, polylactide, copolymers of lactide and glycolide, polydioxanones, polycaprolactones, copolymers of dioxanone and of caprolactone and of trimethylene carbonate, gelatins, monosaccharides such as glucose and mannose, and polysaccharides such as carboxymethyl cellulose and oxidized cellulose typified by Surgicel®, starches, sucrose, suitably in the form of confectioner's sugar, alginic acid, hyaluronic acid, chitosan and its acetyl derivatives, and the like, as well as absorbable glasses, and the like. In addition, certain biologically active materials such as bioglasses (discussed in more detail in connection with Component 4 below), which may not be considered as absorbable in the usual sense, can be used in finely powdered form as Component 1. For example, absorbable polymers having an average particle size of about 25 microns will form a useful, stable absorbable hemostatic putty when mixed with, for example, tocopheryl acetate or the triglyceride oils, especially the castor oil, of U.S. Pat. No. 4,439,420. Thus, any natural or synthetic absorbable polymer that can be reduced to sufficiently small particle size will form a stable, absorbable putty and non-putty if admixed with a suitable, compatible Component 2 vehicle in the proper ratio.

It also has been discovered that absorbable glasses, based upon phosphorus pentoxide (instead of silicon dioxide), and containing alkali or alkaline earth metal oxides such as sodium, potassium, calcium and magnesium oxides as the network polymer, are slowly dissolvable in aqueous media and can be used as Component 1. In addition, such compounds may be used as absorption accelerants, in which case, they may, but need not, be used in as finely powdered a form as when they are used as Component 1. U.S. Pat. No. 4,612, 923 refers to the preparative prior art concerning these glasses as well as their application as additives for strength reinforcement and stiffness enhancement for synthetic absorbable surgical devices. When the 325 mesh glass described in Example 1 of U.S. Pat. No. 4,612,923 is further pulverized to average particle sizes below 50 microns, the resulting fine powder forms a medically useful absorbable putty when admixed with the vehicles described in U.S. Pat. No. 4,439,420 (incorporated herein by reference) and in this specification. The rate of aqueous dissolution (absorption) of such glasses can be increased by increasing the proportion of alkali metal oxides and decreased by increasing the proportion of alkaline earth metal oxides.

This novel approach, discussed above, i.e., forming useful absorbable putties and non-putties by drastically reducing the particle size of the bulking vehicle Component 1, overcomes many of the difficulties of the prior art, especially, e.g., those of synthetic absorbable polymers as bone hemostatic agents.

Component 2

As the second component, i.e., the organic liquid, there may be mentioned, as illustrative, several classes of materials that have not been heretofore employed as dispersing vehicles for preparing medical compositions such as putties or non-putties, although it should be emphasized that even materials already known as dispersing vehicles may be employed. Component 2 acts as the vehicle for dispersing or suspending Component A, the analgesic, and in this aspect of the invention, Component 2 is a biocompatible, essentially anhydrous organic liquid which facilitates the admixture with Component 1 to form the putty or non-putty mass. Though not preferred, Component 2 may be solid if it comprises a separately supplied organic liquid vehicle (a liquefying agent, as more fully discussed below). The term "Component 2" is meant to apply to such a case as well.

While Component 2 is usually water immiscible it may also be water miscible. The important consideration is that it be either anhydrous or essentially anhydrous so as to produce an anhydrous or essentially anhydrous final pain relief composition. In this regard, it is appropriate at this point to illustrate what is meant by "essentially anhydrous". The preferred compositions of the invention are devoid of water except perhaps water that is present by absorption from the atmosphere. Thus, it is preferred that each of the Components used to make up the final composition be themselves devoid of water.

Under some circumstances however, minor amounts of water can be tolerated, and even desirable, in the Components or the final composition for various reasons. Thus, amounts of water ranging up to about 10% by weight of the entire composition, would be acceptable. Compositions with zero percent of water, except for absorbed water, would be considered anhydrous while compositions containing up to about 10% water would be considered essentially anhydrous herein. Components should not contain so much water as to yield a final composition having more than about 10% water. Preferably, the compositions of the present invention have less than 5% water and most preferably zero percent added water (except absorbed water). In the latter case, they would be considered "anhydrous" as that term is normally used in the art.

To aid in understanding the terms used herein and to help differentiate this aspect of the invention from that of the prior art, it would, perhaps, at this point, be useful to emphasize the nature of the chemical entities referred to in this Specification by briefly reviewing relevant classical chemistry terminology to ensure the appropriate chemical distinctions are understood.

Carboxylic acids are substances defined by the attachment of an OH group to a carbonyl function through a covalent bond. As a result, carboxylic acids possess physical and chemical properties totally distinct from substances containing either the carbonyl functionality (e.g., aldehydes, ketones) or the hydroxyl functionality (alcohols). The same distinction holds true for substances containing both the carbonyl and hydroxyl groups not directly attached through a covalent bond, such as hydroxyacetone, which displays both ketone and alcohol properties, but not carboxylic acid characteristics. Carboxylic acids always combine a carbonyl and an OH group and have acidic characteristics, but the OH group does not have the characteristics of the hydroxyl group of an alcohol. A monocarboxylic acid would, therefore, not be described as a monohydroxy compound. To illustrate this, consider acetic acid and ethanol which are both two-carbon compounds containing an OH group. In acetic acid, the hydrogen atom of the OH group is liberated as an ion in water, whereas in ethanol, the hydrogen atom of the hydroxyl group is not so liberated. Thus, carboxylic acids dissociate and form carboxylate salts with bases, e.g., calcium stearate, a distinctive property that clearly differentiates the OH group of carboxylic acids from the hydroxyl group of alcohols that do not dissociate to form salts with bases. Thus, it would be entirely incorrect to characterize a carboxylic acid as an alcohol, a monohydric alcohol, or some such term since it is, in no chemical sense, an alcohol. Nor could a polycarboxylic acid be referred to as a polyalcohol, or a polyhydroxy compound or a polyol simply because it contains carboxylic OH groups. Such groups are not characterized as alcohols. An example of these distinctions is illustrated by considering the well-known molecule, citric acid. This substance has three carboxylic groups and one hydroxyl group in the same molecule. Citric acid is a monohydroxy (monohydric) alcohol as well as a polycarboxylic acid. The fact that citric acid contains three carboxylic OH groups does not classify this monohydroxy compound as a polyhydroxy compound. Because of the major differences in reactivity, synthesis and reactions, in every textbook of organic chemistry, the chemistry of alcohols always is considered in a separate chapter from the chemistry of carboxylic acids.

Alcohols may be regarded either as hydroxyl derivatives of hydrocarbons or as alkyl derivatives of water. They are typified by the R—OH structure where R is an alkyl group. In contradistinction to the readily ionizable hydrogen atom of the carboxylic acid hydroxyl group, the R—OH hydrogen atom is virtually unionized in water. On this basis, aliphatic alcohols are considered neutral rather than acidic. One or more hydroxyl groups may be appended to a hydrocarbon moiety so that, for example, propane may have one hydroxyl group (propyl alcohol), two hydroxyl groups (propanediol or propylene glycol) or three hydroxyl groups (propanetriol or glycerol). Propylene glycol and glycerol are simple examples of polyols. Polysaccharides, such as hyaluronic acid, contain many hydroxyl groups on each monomer unit and are correctly termed polyols. Alcohols may have short alkyl chains such as methyl alcohol, ethyl alcohol, propyl alcohol, etc., or they may have longer alkyl chains such as lauryl alcohol, myristyl alcohol, etc. It is of critical importance to note that lauric acid ($C_{11}H_{23}COOH$, a fatty acid) and lauryl alcohol ($C_{12}H_{25}OH$, a fatty alcohol) are completely different molecules in oxidation state and functionality, even though they both contain twelve carbon atoms.

Esters are commonly derived from the reaction of a carboxylic acid with an alcohol and can be converted back to the original carboxylic acid and alcohol by hydrolysis. Thus, acetic acid and ethyl alcohol are combined in the esterification process to form ethyl acetate and water. The term fat (or vegetable or animal oil) is confined to esters of a variety of long chain saturated or unsaturated fatty acids with glycerine (glycerides). Oils, cited in the prior art as vehicles for preparing putty-like materials, are exclusively glycerides, e.g., castor oil, sesame oil, olive oil, etc., as well as simple fatty acid esters such as ethyl laurate. What never have been proposed in the prior art as vehicles for preparing putty-like substances, are free liquid fatty carboxylic acids such as the saturated caprylic acid and the unsaturated oleic acid. Most important, the use of esters of fatty alcohols with low molecular weight mono- or polycarboxylic acids, e.g., lauryl acetate (the ester of lauryl alcohol and acetic acid) are completely novel for the preparation of putty-like materials and are chemically distinct from the prior art cited ethyl laurate (the ester of lauric acid with ethyl alcohol).

Returning now to the description of the Components of the present invention, more particularly Component 2, the elements are more specifically described as follows:

Among the many classes of organic liquids that may be used as Component 2, there may be mentioned the following:

As a first class of Component 2, there are one or more absorbable esters of a $C_8$-$C_{18}$ monohydric alcohol with a $C_2$-$C_6$ aliphatic monocarboxylic acid. The monohydric alcohols may be selected from $C_8$-$C_{18}$ alcohols such as octyl alcohol, decyl alcohol, lauryl alcohol, myristyl alcohol, stearyl alcohol, and intervening homologs thereof. The preferred alcohols are the higher aliphatics such as lauryl alcohol, myristyl alcohol, and stearyl alcohol. Illustrative of the useful esters formed with the $C_2$-$C_6$ monocarboxylic acids are lauryl acetate and myristyl propionate.

As a second class of Component 2, there are one or more absorbable esters of a $C_2$-$C_{18}$ monohydric alcohol with a polycarboxylic acid. The $C_2$-$C_{18}$ monohydric alcohols include, in addition to the $C_8$-$C_{18}$ alcohols described in the first class of esters there are the lower aliphatic, $C_2$-$C_8$, alcohols such as ethanol, propanol, butanol, pentanol, heptanol, hexanol, and octanol which yield the corresponding ethyl, propyl, butyl, pentyl, heptyl, hexyl, and octyl moieties. The polycarboxylic acids may be selected from malonic, succinic, glutaric, adipic, pimelic, suberic, azelaic, sebacic, maleic, fumaric, glutaconic, citric, malic acids, and esters of the hydroxy function, if any, of the esterified polycarboxylic acid, especially acetyl citric acid and acetyl malic acids. It will be obvious to those skilled in the art that many combinations of alcohol/acid esters may be selected from the above, but the preferred ones for use in the invention from the monohydric alcohol/polyacid esters are diethyl succinate, dioctyl succinate, triethyl citrate, tributyl citrate, and higher and lower homologs thereof, acetyl triethyl citrate, acetyl tributyl citrate and higher and lower homologs thereof, butyryl triethyl citrate, diethyl malate, di-pentyl malate, and acetyl diethyl malate, and higher and lower homologs thereof.

Another class of materials, suitable as Component 2, are the higher $C_8$-$C_{12}$ up to about $C_{30}$ and preferably liquid or liquefiable monohydric alcohols such as octanol and decanol. An especially surprisingly suitable embodiment of this class is the aromatic alcohol tocopherol (Vitamin E) in its optically active or racemic forms and in any of the alpha, beta, gamma or delta forms, as well as liquid tocopherol esters (sometimes referred to herein as tocopheryl esters) with a $C_2$-$C_{10}$ aliphatic monocarboxylic acid, a polycarboxylic acid or mixtures thereof. Useful are the tocopherol esters such as acetates, butyrates, caproates, caprylates, caprates, and intervening homologs thereof, and polycarboxylic acid ester such as those mentioned in the previous paragraph, especially esters of succinic, citric, and malic acids, with succinate being preferred. Tocopherol acetate is also useful as an elution control agent (Component B).

Another class of materials, useful as Component 2, are hydrocarbons having from about 10-14 carbons atoms. For example, decane and dodecane are suitable.

Another class of materials, useful as Component 2, are the liquid or liquefiable saturated or unsaturated, free carboxylic acids such as the non-esterfied fatty acids, oleic, linoleic, caprylic, capric, and lauric. In this class, the normally liquid, saturated fatty acids would be suitable but may not be desirable because of their unpleasant odor. Some low melting saturated free-fatty acid mixtures that form a lower-melting eutectic mixture which is liquid-at-room-temperature may also be suitable. One advantage of saturated free-fatty acids lies in their improved stability to radiation sterilization whereas the unsaturated acids, e.g., oleic, may require radiation sterilization in an oxygen-free container. Higher homologs of solid acids can also be used in admixture with Component 1 in the presence of a liquefying medium or other suitable component. Any compatible liquid may be used as long as it ensures the liquefaction of Component 2 and is biocompatible as well.

Another class of materials, useful as Component 2, are ethers of the simple dialkyl ether class and alkyl aryl ether class as well as cyclic polymers of alkylene glycol e.g., ethylene glycol, known as crown ethers, all having boiling points greater than about 80° C. such as di-n-butyl ether, di-n-hexyl ether, di-n-octyl ether, and unsymmetrical ethers such as ethyl hexyl ether, ethyl phenyl ether, and the like, or random copolymers of ethylene oxide and propylene oxide, but preferably block (non-random) copolymers of ethylene oxide and propylene oxide in various ratios of ethylene oxide to propylene oxide and various molecular weights, preferably from 1000 to 10,000, (Pluronic®). They are available in liquid or solid form. The preferred form for use in the present invention are the liquid Pluronic® which are characterized by their manufacturer (see below) with the prefix "L". Solid forms of Pluronic® characterized as "F" for flake or "P" for powder may be dissolved, dispersed or suspended in the liquid Pluronic® or if desired, used with another liquefying agent. Illustrative of suitable materials are those shown below in the Examples. In addition to their suitability for use as a Component 2, they may also be used as an absorption accelerants. They are available under the trade name Pluronic® from BASF Corp. Mt. Olive, N.J. 07828.

Another class of materials, useful as Component 2, are symmetrical and unsymmetrical dialkyl ketones and alkyl aryl ketones having boiling points greater than about 80° C. such as methyl propyl ketone, diethyl ketone, methyl butyl ketone, ethyl propyl ketone, methyl pentyl ketone, and 2-octanone, 2-nonanone, 2-decanone, and methyl phenyl ketone.

Another class of materials useful as Component 2 are selected from a member of the group consisting of polyhydroxy compounds, polyhydroxy compound esters, solutions of polyhydroxy compound, and mixtures thereof, and fatty acid esters. Preferred among these are the liquid polyhydroxy compounds selected from the group consisting of acyclic polyhydric alcohols, polyalkylene glycols, and mixtures thereof. Specific examples of the foregoing are ethylene glycol, diethylene glycol, triethylene glycol, 1,2-propanediol, trimethylolethane, trimethylopropane, erythritol, pentaerythritol, polyethylene glycols, a liquid solution of a fatty acid monoester of glycerol such as glycerol monolaurate. Solids among the foregoing may be dissolved or dispersed in a suitable solvent medium such as propylene glycol, glycerol, monoacetin, diacetin, liquid polyethylene glycol, and mixtures thereof. As glycerides, there may be mentioned monoglycerides, e.g., glyceryl acetate, glyceryl stearate, homologs thereof, and the like, diglycerides such as glyceryl diacetate, glyceryl dicaprate, dibutyrate, dilaurate, and the like, and triglycerides such as olive oil, castor oil, almond oil, sesame oil, cottonseed oil, corn oil, cod liver oil, safflower oil and soya oil. It should be noted that the foregoing polyhydroxy compounds may also be used, if desired, as absorption accelerants.

As a statement of general applicability, it should be noted that Component 2 materials which are liquid at room temperature are the preferred substances for Component 2, and since they are liquids, a liquefying agent is not necessary. Also useful as Component 2 substances, however, are compounds which are solid at room temperature. In such cases, especially when putties are desired, a solid Component 2 is converted to a liquid form preferably before, but also during, or after admixture with Component A and then Component 1, through the use of an absorbable biocompatible liquefying agent capable of liquefying, solubilizing, dispersing or suspending Component A therein. By "liquefying agent" as used herein, is meant an agent, such as a suitable organic solvent, which can solubilize disperse or suspend Component A and then be blended with the solid Component 2. Other agents may be used, even though the agent may not be considered an organic "solvent" in the usual sense of that term, or an agent which can liquefy the solid, such as heat, or which can disperse the solid in a liquid as a dispersion so as to aid in the formation of a homogenous putty, cream or paste-like mixture. The particular agent used will, of course, depend upon the nature of Component 2 and Component A used in the particular formulation. Suitable agents are materials similar to Component 2 though not precisely described herein as Component 2.

The foregoing novel concepts and compositions especially those utilizing the esters of monoalcohols with the mono- or polycarboxylic acids described above, provide an absorbable bone hemostatic implant with the releasable analgesic. The novel utilization of relatively low molecular weight, non-toxic and rapidly degradable simple esters such as diethyl succinate and triethyl citrate have been found to provide superior alternatives to the much higher molecular weight fatty acid triglycerides, e.g., castor oil, for Component 2. This aspect of the invention thus permits one to avoid, if desired, both the art-known version of Component 2, i.e. hydrophobic, slowly absorbed esters such as the triglycerides typified by the ricinoleic acid triglyceride, castor oil, as well as by fatty acid esters such as isopropyl myristate.

These art-known putty compositions containing the art-known Component 2 materials, such as those of U.S. Pat. No. 4,439,420 can, however, be used to obtain useful pain relief compositions of the inventions in any case but especially in osteogenic bone hemostatic materials in accordance with the following aspect of the invention. It has been discovered that, when it is desired to have a bone hemostatic composition having osteogenic properties albeit with slower absorption characteristics, the art-known composition may be improved by the addition of osteogenic materials, e.g., demineralized bone matrix (DBM), mineralized bone matrix (MBM), hydroxyapatite, tri-calcium phosphate, or growth factors such as bone morphogenic protein (BMP) and platelet derived growth factor (PDGF), as will described below.

Preferred for use as Component 2, in specific embodiments are the following: tocopheryl acetate, triethyl citrate, liquid block copolymers of ethylene oxide and propylene oxide having a molecular weight of about 1900 to about 8000 (Pluronic® L-35, molecular weight 1900, is especially preferred), and a blend of Pluronic® L-35 and F-68 (a flake form of Pluronic®).

Component A

Component A is a critical ingredient of the invention, namely an analgesic having local pain-relieving activity suitable for internal relief of pain as described above. It does not matter whether or not the anesthetic is normally an injectable or systemically used analgesic, provided it has local (topical) pain-relieving activity when implanted at the surgical site. These are sometimes referred to herein and the Examples which follow as "the analgesic component". The analgesics useful in the invention are preferably those that exist in free base form (which includes analgesics with moieties connected through ester or amide linkages) and in the acid addition salt form thereof. Illustrative of these are analgesics having the "-caine" suffix included among which are, benzocaine, bupivacaine, dibucaine, lidocaine, mepivacaine, prilocaine, procaine, chloroprocaine, etidocaine, tetracaine, xylocalne, and propivacaine. As acid addition salts there may be employed the hydrohalides such as the hydrochloride, the hydrobromide, and the like. Preferred are lidocaine and lidocaine hydrochloride.

There also may be employed numerous other analgesics which have local pain-relieving activity such as the non-steroidal anti-inflammatory compounds such as ibuprofen, aspirin, acetaminophen, naprosyn and the like, non-opioids such as fentanyl and pain-relieving prostaglandins. The actual drugs used are not especially limited provided they have local pain-relieving effect at the site and are biocompatible, i.e., not intolerably toxic, at the dosages used.

Component B

There may be added materials which alter the elution rate of the analgesic from the putty. For example, it has been found that the addition of hydrophobic, biocompatible, absorbable materials, e.g., esters of fatty acids or fatty alcohols such as ethyl laurate or lauryl acetate and tocopherols, such as tocopheryl acetate, retard the elution of anesthetic compounds from the putty. On the other hand, the addition of more hydrophilic additives such as tricalcium phosphate, hydroxyapatite, DBM, or lecithin cause an increase in the elution rate of anesthetics from the putty. Hydrophobic compounds may be added up to concentrations of about 20% while up to 40% of hydrophilic additives are effective in increasing the rate of elution.

Component 3—Optional

Component 3, is optionally included as an absorption accelerant and may even be used to control the kinetics of absorption by physically assisting in the disintegration of the implanted mass. Accelerants used in the prior art may be used if they are not toxic or otherwise bioincompatible. One or a combination of such prior art compounds as Carbowax®, Pluronic®, (See discussion under Component 2 supra and discussion below) and glycerine, propylene glycol, lecithin, betaine, and polyhydroxy compounds such as hyaluronic acid, carboxymethylcellulose and chitosan and its acetyl derivatives may be used as absorption enhancers in the compositions of the invention, with the above caveat.

It is preferred, however, to use for this purpose, other materials which are swellable or soluble and absorbable, such as either soluble or insoluble natural or synthetic polypeptides, exemplified by purified, powdered insoluble fibrillar, but swellable collagens, the more rapidly absorbable soluble tropocollagens such as Vitrogen® and the more rapidly absorbable cold and hot water soluble polypeptides, e.g. the gelatins. Lecithin and octylphenyl ethoxylates, such as Triton® R X-100, may be used as biocompatible surfactants to aid in swellability. Polyvinylpyrrolidone and other soluble, absorbable polymers such as the block copolymers of ethylene oxide and propylene oxide discussed supra in connection with Component 2, and relatively hydrophilic polypeptides, e.g., polyaspartic acid, polyglutamic acid, and their salts are also functional in this context. The compositions of the present invention may contain, as the Component 3, insoluble, fibrillar collagen, soluble collagen, gelatin, octylphenyl ethoxylates (e.g. Triton® X-100), the block or random copolymers of ethylene oxide and propylene oxide, polyvinylpyrrolidone or absorbable phosphorus pentoxide-based glasses or stable mixtures of the foregoing.

Particle sizes in the range of about 200-500 microns produce suitable results although larger or smaller particle sizes may be employed depending on the desires of the end user. Gelatin, PVP and other polymers have been used in the demineralized bone art as thickening additives but not as absorption accelerants. The thickening properties of gelatin vary directly with the Bloom number of the gelatin. Gelatin having Bloom numbers ranging from 100-300 are suitable in the compositions of the invention, although values above or below those numbers may be employed if the resulting product is acceptable to the end user.

Illustrative of some suitable proportions of the foregoing Components which produce compositions having the properties described above, are the following (based on the weight of final composition):

Component 1. From about 5 to 80%, preferably about 20 to 60%.

Component 2. From about 5 to about 70%, preferably about 20 to 60%.

Component A. A pharmaceutically effective amount, suitably from about 5 to 25%, preferably about 10 to 20% by weight.

Component B 0 to about 40%.

Water 0 to about 10%.

While the foregoing discussion has been presented largely in the context of materials having the consistency of a putty, in some applications it may be desired to have a relatively less viscous or less cohesive composition or even a more viscous, more cohesive composition. For example, it may be desired to place the composition of the invention into a void in the bone (drilled or otherwise formed, e.g., hairline fractures) into which a putty of high viscosity can be applied only with difficulty. A less viscous form of the putty compositions of the invention would be a desirable alternative. All one needs to do is modify the proportions presented herein to allow for a higher or lower liquid concentration or add a compatible liquid diluent to achieve this purpose. Using this approach, an injectable form of the material can be obtained as well. Other less cohesive strength, non-putty compositions, such as creams, ointments, gels, lotions, and the like previously referred to, may be prepared in the same manner.

Component 4—Optional

Included in the products described above are suitable pain-relieving products which also may allow the growth of bone at the bone wound site. Thus, they are osteoconductive. A desirable aspect of the invention is to make the product osteoinductive as well, that is, to provide the product with Component 4, a bone growth-inducing material in an amount effective to induce bone growth. Thus, the inclusion of osteogenic materials such as growth factors, e.g., Platelet Derived Growth Factor (PDGF), Transforming Growth Factor beta (TGF-beta), Insulin-Related Growth Factor-I (IGF-I), Insulin-Related Growth Factor-II (IGF-II), Fibroblast Growth Factor (FGF), Beta-2-Microglobulin (BDGF II), bone morphogenic protein (BMP), and combinations thereof stimulate osteogenesis to varying degrees. Other bone growth-inducing materials such as demineralized bone matrix (DBM), osteonectin, osteocalcin, osteogenin, and combinations thereof, mineralized bone matrix (MBM) tri-calcium phosphate, as well as bioactive glasses, render the hemostatic product suitably osteogenic.

When used, a suitable amount of osteogenic material to be added to the compositions of the present invention ranges from about 0.001 to about 60% depending upon the material and preferably about 0.001 to about 40% by weight. When used as Component 4, i.e., as an osteogenic material, it is preferred to use certain agents such as DBM or mineralized bone in the form of larger average particle sizes. Suitable larger average particle sizes are in the range of about 0.05 to 10 mm preferably about 0.1 to 5 mm and most preferably about 0.5 to 1 mm. However, the use of Component 4 in smaller or larger particle sizes or in higher or lower amounts will also be suitable if the requirements of the ultimate user are satisfied.

With regard to the relative amounts of osteogenic material to be used in a composition of the invention, one would use a bone growth-inducing effective amount, by which is meant material adequate in amount and form to be osteoinductive in the composition. The amount used may vary depending upon the efficacy of the osteogenic agent and the average particle size of the solid material. For example, growth factors such as BMP, Platelet Derived Growth Factor (PDGF) and the like are effective in fractional weight percent concentrations, whereas effective amounts of DBM, and mineralized bone matrix, are usually in higher weight percent concentrations, e.g., about 10% to about 50% or higher, and preferably in somewhat larger average particle sizes than those used in Component 1.

The addition of the bone growth-inducing material improves not only the compositions of the invention, but also improves the prior art hemostatic formulations to yield novel compositions therewith. Such additions will render these hemostatic formulations osteogenic as well. It is believed that the presence of the osteogenic material will also improve osteoconductive properties because the relatively large particles tend to "open up" the putty structure, thus providing spaces into which induced bone may proliferate.

The type of prior art hemostatic formulations which will especially be improved by such addition are the ones disclosed in U.S. Pat. Nos. 4,439,420 and 4,568,536 each of which is incorporated herein by reference for all purposes. Thus, the present specification and claims are to be read as though the complete specification and claims of the aforementioned patents were reproduced herein verbatim. For purposes of convenience, the formulations of those patents may be generally characterized as comprising an absorbable hemostatic composition for use in the control of osseous hemorrhage, comprising: a component comprising a biocompatible fatty acid salt, the cation of said fatty acid salt being selected from the group consisting of calcium, magnesium, zinc, aluminum, lithium and barium and a component comprising a body absorbable biocompatible base selected from the group consisting of ethylene oxide/propylene oxide block copolymers, polyhydroxy compounds, polyethylene glycols and methoxypolyethylene glycols, triglycerides and fatty acid esters, and an optional absorption enhancing agent. Thus, in this aspect of the invention, the bone growth-inducing materials are added to the above prior art formulations to produce an osteogenic hemostatic material as well as an osteoinductive bone defect filling material.

Other Optional Ingredients

To any of the compositions described infra, may be added a pharmaceutically effective amount of an anti-infective agent, either alone or bound to a substrate to slow its release. Illustrative of such anti-infective materials are antibiotics such as tetracycline, vancomycin, cephalosporins, and aminoglycosides such as tobramycin and gentamicin, alone or bound to collagen, for example, as well as Tricolsan, iodine, alone, or as a PVP complex, colloidal silver, silver salts, alone or bound to a carrier such as gelatin, collagen, and the like.

Other materials, such as vasoconstrictors and blood clot-inducing agents, e.g., epinephrine, tannic acid, ferrous sulfate, and the double-sulfates of a trivalent metal and a univalent metal such as potassium aluminum sulfate and ammonium aluminum sulfate; anti-neoplastic agents such as methotrexate, cis-platinum, doxorubicin, and combinations thereof, radionuclides such as Strontium 89, and the like; analgesics as referred to infra, such as benzocaine, lidocaine, tetracaine, fentanyl (a potent non-opioid), and the like; anti-inflammatory substances such as the non-specific ibuprofen and aspirin, or the COX-2 specific inhibitors such as celeboxib; radiopaque substances such as iodo compounds, e.g., ethylmonoiodo stearate available as Ethiodol® (Savage Laboratories), and barium salts such as barium stearate, may be added to the formulations in amounts which are effective to achieve their therapeutic or diagnostic purposes. Depending upon the characteristics of the colorant selected, colorants such as gentian violet, D&C Violet #2, and D&C Green #6 are suitable.

In some embodiments of the invention, it may be desirable to intimately admix water with the compositions of the invention. The presence of a small amount of water, of the order of up to ten percent or more, aids in a variety of ways among which is changing the tactile quality of the composition. In this regard, the resulting compositions often impart a sensation of reduced coarseness over what may have existed in the compositions without the water addition. In some instances, it is desirable to provide a putty-like formulation or a less dense non-putty formulation having a cohesive strength less than that of a putty, such as a cream, a paste, or other such materials as previously set forth herein, based upon water or other aqueous liquids rather than on more hydrophobic vehicles.

Bulking agents such as the metal fatty acid salts, e.g., calcium stearate and other non-wettable bulking agents described herein, are not wetted by water and do not provide putty-like (or less dense) compositions with water. We have found, however, that the treatment of the bulking agent with a small amount of surface-active material, e.g., lecithin, a Pluronic® such as Pluronic L-35®, renders the unwettable bulking agent sufficiently wettable to enable the preparation of a suitable fatty acid salt-water formulation when Component 2 is an aqueous vehicle. Suitable aqueous vehicles are water, saline, various biocompatible buffer solutions, various body fluids, such as blood, serum, blood component concentrates, and the like.

If water soluble anesthetic salts are used in the formulation, they may be dissolved in a minimal quantity of water prior to adding to the other Components of the formulation. While the above putties have less resistance to irrigation compared with the putties prepared using more hydrophobic materials, they have applications in bone defect repair where more rapid disintegration of the implant is desired. Non-ionic, cationic, and anionic surfactants are suitable, although virtually any biocompatible surfactant may be used as exemplified by dodecyl trimethyl ammonium chloride, sodium lauryl sulfate, nonoxynol-9, the Tweens, e.g., polyoxyethylenesorbitan monolaurate, Tergitol-7, i.e., sodium heptadecyl sulfate, and the antimicrobial surfactant, 1-lauryl-3-ethylbenzo-triazolium bromide, and the like. Non-putty-like compositions, such as creams, pastes, and the like, may be prepared by using additional quantities of water or Component A. This is especially useful during surgical procedures when it is desired to form a putty- or cream-like composition using, for example, blood instead of water.

The foregoing discussion relating to the use of blood clot-inducing agents in the present invention illustrates the embodiment wherein the compositions are capable of chemical hemostasis in use. That is, the addition of a styptic material to the compositions of the present invention, whether those compositions are mechanically hemostatic or not, yields compositions having the ability to act as chemical hemostatic materials. Thus, an already mechanically hemostatic putty can be made more efficiently hemostatic by adding a blood clot-inducing material. Similarly, a lower cohesive strength cream or paste, which may lack significant mechanical hemostatic properties, can be made hemostatic by the addition of a blood clotting material. An example of the latter is the application of a thin layer of a vasoconstrictor-modified paste of the invention to a bleeding acetabulum in hip surgery.

The components described above, when added together in suitable proportions, yield useful, putty-like and non-putty like agents having, to varying degrees, many favorable characteristics. Various combinations of the components may require different times and temperatures in the preparation process in order for the putty-like characteristics to develop. For example, some materials such as finely divided hydroxyapatite may take longer than other components to achieve the putty-like state. In general, the putty-like compositions of the present invention are absorbable within a reasonable time, usually within 30-60 days although absorption times may be extended to several months or longer for some applications. They are moldable and shapeable by hand at ambient temperatures, handle well in presence of blood, and are washable with saline. They sometimes are tacky to the touch, but do not stick to any great degree to surgical gloves, wet or dry. They can be radiation sterilized when radiation-sensitive material such as DBM or certain antimicrobials are not present.

The actual proportions of the materials selected will vary depending upon the materials themselves, the number of components used, and the end use desired for the final putty composition. The user will be guided initially by the requirement for the desired viscosity, cohesive strength, and consistency to be obtained, i.e. compositions ranging from flowable liquid consistencies to consistencies of creams, pastes, ointments, gels, and the like to the more cohesive putty-like consistencies, while maintaining other characteristics desired in the ultimate use of the component. For example, for a number of procedures, it is important to be able to secure the analgesic composition to the site from which the pain originates. In orthopaedic surgery, compositions are provided to adhere to the surface of the bone as it releases the analgesic to the local environment. In general surgery, however, there usually is no hard surface to which putty-like, or even higher viscosity, compositions can adhere. Such difficulties are addressed by this embodiment. Specifically, it has been found that a sieve-like or fabric-like or felt-like or non-woven structure can be uniformly impregnated with such materials containing analgesic drugs to yield a fabric-putty laminate containing analgesics. Of course, other drug substances such as for example, antimicrobial, anti-inflammatory and anti-cancer agents as well as growth stimulating agents such as PDGF, etc., described herein, can be incorporated in the devices of this embodiment of the invention.

While the solid component of this invention is universally absorbable to avoid long-term residence of solid foreign bodies, the fabric component may be absorbable or non-absorbable, depending on the surgical need. For example, a fabric-putty laminate serves to provide a standardized amount of drug per unit area as well as a means for securing the device to the area of need (if simple placement of the laminate of this invention on or in the tissue is not adequate) by using tack sutures or staples to attach the fabric component to the adjacent tissue.

For procedures involving the need for permanent support or reinforcement such as hernia repair, a non-absorbable fabric may be indicated. Thus, in the post-operative stage, as the analgesic becomes exhausted and the putty absorbs, the remaining non-absorbable fabric serves to permanently reinforce the repaired defect. Fabrics such as those prepared, for example, by knitting polyester, polypropylene or polyethylene fibers, or non-woven or felt-like fabric are examples of useful materials since they are presently and successfully used in other body-compatible procedures. Thus, the present invention is useful with any type of fabric, absorbable or non-absorbable, provided the fabric is compatible with the exigencies of the particular surgery being performed. In fact, the substrate need not be a "fabric" in the usual sense that the word "fabric" is normally used. For example, the substrate may be a non-woven or felt-like fabric upon which the compositions are applied to or impregnated into.

For procedures not requiring permanent reinforcement, absorbable fabrics such as those made from synthetic absorbable polymers such as polyglycolic acid and natural absorbable polymers such as collagen, alginates, and the like, are applicable. In this case, the entire device is absorbed after its drug delivery function has been fulfilled.

This aspect of the invention utilizes not only creams and putties as the analgesic carrier vehicle, but also other compositions which can be applied to a substrate and be supported thereon. The analgesics employable herein can be any which are internally tolerated such as those previously described herein. Illustrative of others that may be used are non-steroidal anti-inflammatory compounds such as Torodol®, ibuprofen, aspirin, acetaminophen and the like.

For many uses, a substrate in the form of a netting, gauze, fabric, felt or non-woven structure is suitable. The form may be rigid, flexible, flat or contour-shaped as desired or required by the procedure. One may visualize a shape in the form of, for example, a gauze-like substrate, fashioned out of the appropriate material to which a layer of the composition described herein may be applied, much as in the manner that a layer of Vaseline® is applied to a cotton gauze. There is no particular limitation on the substrate as long as it can support the analgesic composition and is body-compatible.

The composite or laminate of this aspect of the invention is thus amenable to use in a variety of procedures, of which the following are typical, but only illustrative:

a) collagen substrate covered with a putty comprising ibuprofen as the analgesic, applied in orthopaedic surgeries such as knee, hip and shoulder replacements.

b) absorbable polymer mesh bearing a putty composition as the analgesic-delivering composition containing any of the "-caine" analgesic compounds in free base or acid addition salt for or combinations thereof, applied to cut bone to staunch bleeding and provide post operative pain relief in a hernia operation, for example:

c) a knitted fabric of an absorbable material such as Vicryl® carrying an impregnated coating of a thick paste or cream composition of the invention comprising an analgesic wherein the fabric may be attached or applied to, or draped over surgically exposed tissue.

The compositions described in this Specification, when used surgically, must be sterile. All, except those noted below, are radiation sterilizable using, for example, a standard cobalt-60 radiation source and a nominal dose of 25 kGy. Exceptions are formulations containing radiation-sensitive additives such as demineralized bone matrix, bone morphogenic protein, certain antibiotics, unsaturated molecules such as oleic acid and the like. When such materials are used, sterility may be achieved by radiation-sterilizing the bulk putty-like or non-putty like material and aseptically adding the sterile radiation-sensitive additive followed by aseptic packaging.

The compositions described in this Specification may be sterile or sterilizable and may be packaged in several formats. The packages themselves may be sterile or sterilizable. The compositions may be packaged as an amorphous (i.e., shapeless or having no definite shape) material such as a paste, cream, or putty, or in the shape of its container. They may be shaped generally as a parallelepiped or as a generally rounded form, examples of the former being small brick-shapes or slabs (in the shape of a stick of chewing gum), and examples of the latter being cylindrically shaped, egg-shaped, or spherically shaped products. Alternatively, when the application permits and the viscosity is suitable, the product can be packaged in a syringe-like or plunger-assisted dispenser expressible or extrudable through an orifice of appropriate cross section and shape. A mechanical assist device similar to that used for caulking may be included. Another package contains the product in a squeezable, deformable tube such as a toothpaste-type tube or a collapsible tube such as those used in caulking applications, with an orifice shaped and sized to dispense any suitable shape onto the surface to be treated. The package may comprise an outer barrier as an overwrap, for example, a peelable blister pouch, to allow aseptic delivery of the package to the sterile field.

The present invention also contemplates methods of use of the compositions of the invention. For example, one embodiment is the method of mechanically controlling the bleeding of bone by the application of an effective amount of any of the compositions of the invention to bleeding bone, wherein the composition has a sufficiently dense consistency, such as in the putty compositions of the invention. In such a case, the composition is a mechanical hemostatic tamponade.

Another embodiment of the method of use of the invention is the method of chemically controlling the bleeding of bone by the application of an effective amount of any of the compositions of the invention, wherein the composition contains a blood clot-inducing agent as heretofore set forth. In the case of putties, the composition is a chemical hemostatic tamponade. Mechanical hemostatic tamponades of the invention which also comprise a clot-inducing agent will act as both a mechanical hemostat and a chemical hemostat.

Another method of the invention is the method for inducing the growth of bone in a bone defect by applying an effective amount of any composition of the invention containing a bone growth-inducing agent, to the affected area of bone, especially when the composition includes a bone growth-inducing material such as DBM, mineralized bone matrix, bone morphogenic protein, hydroxyapatite, or the like. Another method is the method for treating an infection in or around a bone by applying an effective amount of any composition of the invention containing an anti-infective agent, to the affected area of bone to be treated.

Another method is the method for destroying cancer cells in or around a bone by applying an effective amount of any composition of the invention containing an anti-neoplastic agent, to the affected area of bone which contains such cells.

Another method is the method for reducing pain from an area in or around a bone by applying an effective amount of any composition of the invention containing an analgesic agent, to the affected area.

Another method is the method for controlling inflammation in or around a bone by applying an effective amount of any composition of the invention containing an anti-inflammatory agent, to the affected area.

Another method is the method for assessing the status of an area in bone to which an implant has been applied by applying an effective amount of any composition of the invention containing a radiopaque agent, to the affected area and thereafter radiographically visualizing the area and making a determination of the status of the area.

Another method is the method for rendering wettable any of the bulking agents used in the invention which may be hydrophobic by treating the bulking agent with a cationic, anionic, or non-ionic surfactant and then making a water-based putty from the treated bulking agent using any source of liquid such as water itself, saline, or body fluids such as blood, serum, or the like.

Other methods are each of the foregoing methods for treating or managing post-operative pain wherein the composition comprises an analgesic.

Those skilled in the art will be aware of the manner in which the compositions are applied and the amount thereof. In some applications, large amounts of the tamponade may be used while in others only small amounts may be required or desired.

The methods and examples provided below are intended to more fully describe preferred embodiments of the invention and to demonstrate its advantages and applicability.

The following examples illustrate specific embodiments of the present invention.

EXAMPLE 1

In this example and in all subsequent examples, unless otherwise indicated, the composition was prepared by mechanical blending of all dry reagents first and thereafter adding gradually any liquid reagents. The composition was "worked" with a spatula at room temperature until the desired consistency was obtained. In some cases, if the material needed additional ingredients to improve the consistency, that material was added and the mixture continually kneaded or "worked" until the desired putty-like consistency was obtained. The components are presented in parts by weight.

| | | |
|---|---|---|
| Component 1 | Calcium stearate | 4 g. |
| Component 2 | Tocopheryl acetate | 3 g. |
| Component 3 | Gelatin | 3 g. |

The sample yielded a putty-like mass with excellent water resistance, physical and hemostatic characteristics and water resistance properties, i.e., it resisted strongly attempts at washing it away under the force of flowing tap water.

EXAMPLE 1 A)

By varying the proportion of the liquid components, the compositions of the present invention can be rendered into states of lower (i.e. more liquid) or higher (i.e. more rigid) viscosities. Illustrative of a lowered viscosity formulation is the following: to the putty formulation of Example 1 is added 3 g. of acetyl triethyl citrate. The resulting product has a cream-like consistency and may be applied, in appropriate circumstances, to bone as a hemostatic agent or as a delivery agent for a variety of additives such as drugs.

EXAMPLE 2

Partial replacement of calcium stearate with bone growth-inducing materials

| a) | | | |
|---|---|---|---|
| | Component 1 | Calcium stearate | 3 g. |
| | Component 2 | Tocopheryl acetate | 3 g. |
| | Component 3 | Gelatin | 3 g. |
| | Component 4 | Hydroxyapatite (6–12 micron particle size) | 1 g. |

The resulting product is a putty-like mass with properties comparable to the product in Example 1. When a small amount of gentian violet sufficient to impart a discriminating light violet color is added to the above formulation, a colored product with the characteristics of the product of Example 1 is obtained.

| b) Complete replacement of calcium stearate with hydroxyapatite. | | |
|---|---|---|
| Component 1 | Hydroxyapatite (6–12 micron particle size) | 2 g. |
| Component 2 | Tocopheryl acetate | 2.5 g. |
| Component 3 | Gelatin | 2 g. |

The composition was allowed to stand at room temperature for 72 hours yielding a product that had the characteristics of the product of Example 1.

EXAMPLE 3

| | | |
|---|---|---|
| Component 1 | Aluminum Palmitate | 5 g. |
| Component 2 | Tocopheryl acetate | 3 g. |
| Component 3 | Gelatin | 3 g. |

The resulting product is a putty-like mass with properties similar to those described for the product in Example 1.

EXAMPLE 3 A), 3 B), 3 C)

The putty-like formulation of Example 3 is rendered into less viscous compositions by modifying the Example 3 formulation as follows:

| | | Ex. 3 | Ex. 3a | Ex. 3b | Ex. 3c |
|---|---|---|---|---|---|
| Component 1 | Aluminum Palmitate | 5 | 5 | 5 | 5 |
| Component 2 | Tocopheryl acetate | 3 | 4 | 6 | 8 |
| Component 3 | Gelatin | 3 | 0 | 0 | 0 |

Formulation 3a has the consistency of a soft putty.

Formulation 3b has the consistency of a thick cream much like cake icing.

Formulation 3c has the consistency of a slowly flowable composition much like cold honey.

Each of them can be applied to bone as a hemostatic agent.

EXAMPLE 4

| | | |
|---|---|---|
| Component 1 | Calcium stearate | 5 g. |
| Component 2 | Tocopheryl acetate | 3 g. |
| Component 3 | Gelatin | 3 g. |
| Component 4 | DBM | 3 g. |

The resulting product has, in addition to hemostatic properties of the product of Example 1, the additional property of osteoconductivity.

EXAMPLE 5

| | | 5 a. | 5 b. |
|---|---|---|---|
| Component 1 | Calcium stearate | 2 g. | 1.3 |
| Component 2 | Triethyl citrate | 1.6 g. | 0.98 |
| Component 3 | Triton ® X-100 | 0 | 0.02 |

The resulting product 5a, was putty-like and had physical characteristics similar to those of Example 1. Product 5b was also putty-like and is more rapidly absorbable than 5a. Triton® X-100 is available from Dow Chemical Co., Midland, Mich.

EXAMPLE 6

| | | |
|---|---|---|
| Component 1 | Calcium stearate | 4 g. |
| Component 2 | Triethyl citrate | 3 g. |
| Component 3 | Gelatin | 3 g. |

The resulting product was putty-like and had physical characteristics useful as a hemostat, but not preferred when compared to the product of Example 5.

EXAMPLE 7

| | | |
|---|---|---|
| Component 1 | Calcium stearate | 2 g. |
| Component 2 | Acetyl triethyl citrate | 2 g. |

The resulting product has excellent putty-like characteristics and physical characteristics comparable to those of Example 1.

EXAMPLE 8

| | | |
|---|---|---|
| Component 1 | Calcium stearate | 0.5 g. |
| Component 2 | Triethyl citrate | 1 g. |
| Component 4 | Hydroxyapatite | 2 g. |

There resulted a low viscosity injectable composition having hemostatic properties.

EXAMPLE 9

| | | |
|---|---|---|
| Component 1 | Calcium stearate | .5 g. |
| Component 2 | Tocopheryl acetate | 2 g. |
| Component 4 | Hydroxyapatite | 2 g. |

There resulted a composition having excellent putty-like characteristics and water resistance.

EXAMPLE 10

| | | |
|---|---|---|
| Component 1 | Hydroxyapatite | 2 g. |
| Component 2 | Triethyl citrate | 2.5 g. |

There resulted a composition which is easily applied to rough bone surfaces with good adhesion and filling characteristics.

EXAMPLE 11

| | | |
|---|---|---|
| Component 1 | Calcium stearate | 3 g. |
| Component 2 | Tocopheryl acetate | 1.0 g. |
| Component 2 | Triethyl citrate | 1.5 g. |
| Component 3 | Gelatin | 2 g. |

The resulting product was a good material with putty-like physical characteristics similar to those of Example 1 and somewhat more sticky than that of Example 1.

EXAMPLE 12

| | | |
|---|---|---|
| Component 1 | Calcium stearate | 4 g. |
| Component 2 | Lauric acid | 4 g. |
| Component 2 | Tocopheryl acetate | .5 g. |

The calcium stearate was blended with melted lauric acid and formed a good putty which, upon cooling, solidified. The solid was then crushed and blended with the tocopherol to yield a good putty.

The resulting product has a putty-like consistency at body temperatures and a somewhat harder consistency at room temperature.

EXAMPLE 13

| | | |
|---|---|---|
| Component 1 | Calcium stearate | 4 g. |
| Component 2 | Triethyl citrate | 4 g. |
| Component 2 | Lauric acid | 4 g. |

The resulting product was putty-like and had physical characteristics similar to those of Example 1 and with somewhat less cohesiveness.

EXAMPLE 14

| | | |
|---|---|---|
| Component 1 | Calcium stearate | 2 g. |
| Component 2 | Dodecane | 1 g. |

The resulting product had good water resistance, was of lower viscosity and compared well with the other physical characteristics of Example 1.

EXAMPLE 15

| | | |
|---|---|---|
| Component 1 | Calcium stearate | 2 g. |
| Component 2 | Octanol-1 | 1 g. |

The resulting product was of lower viscosity and had physical characteristics similar to those of Example 14 but somewhat less cohesive.

EXAMPLE 16

| | | |
|---|---|---|
| Component 1 | Calcium stearate | 2 g. |
| Component 2 | Diethyl succinate | 2 g. |
| Component 3 | Gelatin | 2 g. |

The resulting product was a good putty similar to Example 1.

EXAMPLE 17

| Component 1 | Calcium stearate | 4 g. |
|---|---|---|
| Component 2 | Diethyl succinate | 3 g. |

The resulting product was a good putty which had improved consistency over that of Example 16.

EXAMPLE 18

| Component 1 | Calcium stearate | 4 g. |
|---|---|---|
| Component 2 | Acetyl triethyl citrate | 3 g. |
| Component 3 | Gelatin | 3 g. |

The resulting product was comparable to that obtained in Example 1.

EXAMPLE 19

| Component 1 | Aluminum palmitate | 4 g. |
|---|---|---|
| Component 2 | Tocopheryl acetate | .3 g. |
| Component 2 | Triethyl citrate | 3 g. |

The resulting product was a soft, somewhat translucent putty with good water resistance and good hemostatic characteristics.

EXAMPLE 20

| Component 1 | Calcium stearate | 3 g. |
|---|---|---|
| Component 2 | Tocopheryl acetate | 3 g. |
| Component 3 | Gelatin | 3 g. |
| Component 4 | Demineralized bone matrix | 1 g. |

The resulting product is a putty-like mass with properties comparable to the product in Example 1 and has osteogenic properties as well.

EXAMPLE 21

| Component 1 | Hydroxyapatite | 3 g. |
|---|---|---|
| Component 2 | Tocopheryl acetate | 3.5 g. |
| Component 3 | Gelatin | 3 g. |

In this example, the material initially was soft and oily and lacked coherence. However, upon standing at room temperature for 72 hours, an excellent putty with good water resistance formed. Increasing the amount of tocopheryl acetate by an additional 3 g. yields a paste having a coarseness attributable to the gelatin.

EXAMPLE 22

| Component 1 | Calcium stearate | 3 g. |
|---|---|---|
| Component 2 | Di-n-hexylether | 2.5 g. |
| Component 3 | Gelatin | 2 g. |

The resulting product is putty-like and has good water resistance and physical characteristics similar to those of Example 1.

EXAMPLE 23

| Component 1 | Calcium stearate | 3 g. |
|---|---|---|
| Component 2 | Di-n-pentylketone | 2.5 g. |
| Component 3 | Gelatin | 2 g. |

The resulting product is putty-like and has good water resistance and physical characteristics similar to those of Example 22.

EXAMPLE 24

| Component 1 | Calcium stearate | 3 g. |
|---|---|---|
| Component 2 | Tocopheryl acetate | 3 g. |
| Component 3 | Bovine collagen (powdered) | 3 g. |

The resulting product is putty-like, has good water resistance and physical characteristics similar to those of Example 23. In addition, the putty has a fibrous texture as a result of the fibrous powdered collagen sponge additive present as the absorption accelerant (Component 3).

EXAMPLE 25

| Component 1 | Calcium stearate | 3 g. |
|---|---|---|
| Component 2 | Tocopheryl acetate | 3 g. |
| Component 3 | *Bovine collagen (powdered) containing gentamicin sulfate. | 3 g. |

*CollatampG, available in Europe

There results a hemostatic putty with anti-infective properties.

EXAMPLE 26

| Component 1 | Calcium stearate | 4 g. |
|---|---|---|
| Component 2 | Tocopheryl acetate | 3 g. |
| Component 3 | Gelatin | 3 g. |
| Anti-Infective | Gentamicin sulfate | 120 mg. |

Example 1 is repeated except that 120 mg. of gentamicin sulfate is combined with the dry components before the tocopheryl acetate is added to make a putty. This example demonstrates the preparation of a putty with anti-infective properties.

EXAMPLE 27

| Component 1 | Calcium stearate | 4 g. |
|---|---|---|
| Component 2 | Tocopheryl acetate | 3 g. |
| Component 3 | Gelatin | 3 g. |

Example 1 is repeated except that the gelatin is soaked in 2% aqueous silver nitrate for 2 hours at room temperature, washed with two changes of distilled water and one of acetone and then dried overnight. This preparation has anti-infective properties as a result of the presence of silver/gelatin complexes.

EXAMPLE 28

| Component 1 | Calcium stearate | 4 g. |
|---|---|---|
| Component 2 | Tocopheryl acetate | 3 g. |
| Component 3 | Gelatin | 3 g. |

Example 1 is repeated except that 10 mg of the gelatin is incubated overnight in one ml. of an aqueous solution containing 10 micrograms of lyophilized human bone morphogenetic protein (BMP-2, Sigma-Aldrich) followed by air-drying overnight. The damp gelatin is washed with acetone to remove residual moisture and combined with the remainder of the gelatin to prepare the putty having osteogenic and hemostatic properties.

EXAMPLE 29

| Component 1 | Calcium stearate | 4 g. |
|---|---|---|
| Component 2 | Tocopheryl acetate | 3 g. |
| Component 3 | Gelatin | 3 g. |

Example 1 is repeated except that 0.5 ml of Betadine® (povidone-iodine, 10%; equivalent to 1% available iodine) was mixed into 10 g. of the formed putty of Example 1. The mass turned to a brown color and has anti-infective properties.

EXAMPLE 30

| Component 1 | Micronized polylactic acid | 3 g. |
|---|---|---|
| Component 2 | Tocopheryl acetate | 1.5 g. |

The mixture formed an excellent putty with good water resistance and properties comparable to the product in Example 1.

EXAMPLE 31

The following composition is described in U.S. Pat. No. 4,439,420 as a preferred composition of about 40% calcium stearate, 30% dextran and 30% castor oil. If water is added, the preferred composition is 38% calcium stearate, 28% dextran, 27% castor oil and 7% water (all weights are weight percent). The composition was prepared by mechanical mixing at ambient temperatures to avoid possible degradation of heat-sensitive components.

| Calcium stearate | 4 g. |
|---|---|
| Castor oil | 3 g. |
| Dextran | 3 g. |

The calcium stearate and dextran were dry blended in a 50 ml glass beaker and the castor oil was added with stirring using a spatula. After several minutes of "working" the mixture with the spatula at room temperature, the consistency gradually changed. The mixture became crumbly and, after further working, became putty-like. The addition of a small amount of water (about 1 g.) reduces the gritty nature of the dextran.

EXAMPLE 32

The formulation in Example 31 was modified as indicated below to make a novel, putty-like composition of the present invention. The mass is an effective hemostat and is an effective osteogenic bone defect filler.

| Calcium stearate | 2 g. |
|---|---|
| Castor oil | 1.5 g. |
| Dextran | 1.5 g. |
| DBM (demineralized bone matrix) | 1.5 g. |

The purpose of this example is to show that DBM can be added to the compositions described in U.S. Pat. No. 4,439,420 to obtain a putty-like mass with osteogenic properties.

EXAMPLE 33

| Component 1 | Aluminum Palmitate | 5 g. |
|---|---|---|
| Component 2 | Tocopheryl acetate | 3 g. |
| Component 3 | Gelatin | 3 g. |
| Additive | Methotrexate | .2 g. |

Additive Methotrexate 0.2 g.

The now chemotherapeutic putty is packed into a bone defect following surgical excision of a bone tumor.

EXAMPLE 34

| Component 1 | Aluminum Palmitate | 5 g. |
|---|---|---|
| Component 2 | Tocopheryl acetate | 3 g. |
| Component 3 | Gelatin | 3 g. |
| Additive | Strontium 89 (as a salt) | |

The above formulation, when provided with radioactively effective amounts of Strontium 89, yields a radiotherapeutic putty as described in Example 33.

EXAMPLE 35

| | | |
|---|---|---|
| Component 1 | Pulverized Absorbable Phosphate Glass | 3 g. |
| Component 2 | Tocopheryl Acetate | 1 g. |

A crucible containing sodium dihydrogen phosphate hydrate was heated for 4 hours at about 800 degrees C. and then rapidly cooled. The resulting absorbable phosphorus glass mass then was broken up with a hammer and the fragments pulverized to a fine powder in a rotating ball mill for about 72 hours. The finely pulverized glass (3 g.) was stirred with tocopheryl acetate (1.0 g.) until a putty-like mass formed having good physical properties and water resistance.

EXAMPLE 36

| | | |
|---|---|---|
| Component 1 | Calcium stearate | 3 g. |
| Component 2 | Ethyl laurate | 3 g. |
| Component 4 | Demineralized bone matrix | 1 g. |

The purpose of this example is to show that DBM can be added to the compositions described in U.S. Pat. No. 4,439,420 to obtain a putty-like mass with osteogenic properties.

EXAMPLE 37

| | | |
|---|---|---|
| Component 1 | Hydroxyapatite | 3 g. |
| Component 2 | Isopropyl palmitate | 3.5 g. |
| Component 3 | Gelatin | 3 g. |

Upon standing at room temperature for 72 hours, an excellent putty with good water resistance comparable to that of Example 2 is obtained.

EXAMPLE 38

| | | |
|---|---|---|
| Component 1 | Calcium Stearate | 5 g. |
| Component 2 | Glycerol (USP) | 15 g. |

Three grams of calcium stearate were mixed with 3 gram incremental quantities of glycerol until the mixture displayed a cream-like consistency (total of 15 g. glycerol). At that stage, an additional two grams of calcium stearate were blended into the mixture to obtain a composition having the consistency and appearance of well-beaten egg whites.

EXAMPLE 39

| | | |
|---|---|---|
| Component 1 | Calcium Stearate | 1 g. |
| Component 2 | Tocopheryl acetate | 1 g. |
| Component 3 | Glycerol | .25 g. |

There resulted a relatively soft putty with excellent water resistance.

EXAMPLE 40

| | | |
|---|---|---|
| Component 1 | Sucrose (Confectioner's Sugar) | 3 g. |
| Component 2 | Olive Oil | 2 g. |

This results in a relatively rigid putty which washes away very easily and is useful where low water resistance is desired.

EXAMPLE 41

Three grams of the product from Example 38 above was mixed with 0.75 ml. of deionized water containing 30 ppm of colloidal silver (Source Naturals, Inc., Scotts Valley, Calif. 98006). The resulting hemostatic cream became off-white in color, due to the presence of the anti-microbial silver, and was somewhat less viscous than the original cream.

EXAMPLE 42

| | | |
|---|---|---|
| Component 1 | Calcium Stearate | 4 g. |
| Component 2 | Pluronic ® L-35* (Molecular Wt. 1900) | 0.2 g |
| Component 12 | Water | 2 g |

*Pluronic 588310, Lot WPAW-502B, BASF, Corp. Mt. Olive, NJ 07828-1234

Pluronic 588310, Lot WPAW-502B, BASF, Corp. Mt. Olive, N.J. 07828-1234

The ingredients are combined with stirring until a putty-like mass results. The material is easily dispersed in excess water.

EXAMPLE 43

| | | |
|---|---|---|
| Component 1 | Calcium Stearate | 12.0 g. |
| Component 2 | d,1-alpha Tocopheryl Acetate | 7.5 g. |
| Component 3 | Soya Lecithin Granules | 1.3 g. |

The calcium stearate and lecithin (Archer-Daniels-Midland Ultralec P) were mixed dry and the tocopheryl acetate was then added with vigorous stirring. A putty formed which had good water resistance and handling properties, but which was slightly more tacky than corresponding formulations containing gelatin instead of lecithin.

EXAMPLE 44

| | | |
|---|---|---|
| Component 1 | calcium stearate | 0.6 g. |
| Component 1 | potato starch* | 3.8 g. |
| Component 2 | d,1-alpha tocopheryl acetate | 1.6 g. |

*Razin International, Inc.
6527 Route 9
Howell, New Jersey 07731

The tocopheryl acetate and calcium stearate were mixed together and the starch was then added. The mixture formed a soft, white putty with good water resistance. To prevent the formation of post-operative adhesions, it may be desirable to sterilize the putty using 25 kGy of ionizing gamma radiation from a cobalt 60 source in order to degrade the starch. Alternatively, the starch may be subjected to radiation degradation prior to formulating it into the putty.

The following Examples 45-52 show putty compositions, prepared as in Example 1, having good water resistance and incrementally increasing absorbabilities from slowly absorbable to more rapidly absorbable as the amount of gelatin is increased relative to the amount of calcium salt.

|  | Parts Ca salt | Parts component 2 | Parts - | gelatin-% |
| --- | --- | --- | --- | --- |
| EXAMPLE 45 | 12 Ca stearate | 7.5 tocopheryl acetate | 0 | 0 |
| EXAMPLE 46 | 12 Ca stearate | 7.5 tocopheryl acetate | 2.0 | 10 |
| EXAMPLE 47 | 12 Ca stearate | 7.5 tocopheryl acetate | 3.5 | 15 |
| EXAMPLE 48 | 12 Ca stearate | 7.5 tocopheryl acetate | 5.0 | 20 |
| EXAMPLE 49 | 12 Ca laurate | 7.5 tocopheryl acetate | 4.5 | 20 |
| EXAMPLE 50 | 12 Ca stearate | 7.5 triethyl citrate | 4.5 | 20 |
| EXAMPLE 51 | 0.6 Ca stearate | 1.6 tocopheryl acetate | 5.0 | 70 |

EXAMPLE 52

|  |  | a)parts-% |  | b)parts-% |  |
| --- | --- | --- | --- | --- | --- |
| Component 1 | Ca stearate | 3.4 | 31 | 2.35 | 21 |
| Component 2 | tocopheryl acetate | 3.2 | 29 | 2.21 | 20 |
| Component 3 | Gelatin (150 Bloom) | 4.4 | 40 | 3.04 | 28 |
| Component 4 | DBM | 0 |  | 3.40 | 31 |
|  | TOTAL | 11.0 |  | 11.0 |  |

The resulting product has characteristics similar to the putty of Example 53.

The gelatin in formulation a) is present at 40% by weight and the composition has good putty consistency with good water resistance and absorbability.

When it is desired to obtain a denser formulation that may be used as a vehicle in anchoring pins or screws, such as pedicle screws, to bone in orthopedic procedures, the foregoing formulation a) may be modified by including therein large particle size bone chips and applied to the appropriate bone site. Thus, when 31 parts of DBM, particle size 1-5 mm, are added to 69 parts of formulation a), formulation b) results, comprising 31% DBM and 28% gelatin. The consistency is that of a thick, dense putty into which pins or screws may be placed and anchored into adjoining bone. In time, the osteogenic character of the formulation will allow bone growth around the pins or screws thus permanently anchoring them to adjoining bone structures.

EXAMPLE 53

| Component 1 | Ca stearate | 3.0 g |
| --- | --- | --- |
| Component 2 | tocopheryl acetate | 0.4 g |
| Component 2 | tributyl citrate | 2.3 g |
| Component 3 | gelatin | 2.0 g |

There resulted a putty having very good hemostatic and absorbability characteristics.

EXAMPLE 54

| Component 1 | Ca stearate | 3.0 |
| --- | --- | --- |
| Component 2 | tocopheryl acetate | 0.4 |
| Component 2 | acetyl tributyl citrate | 2.3 |
| Component 3 | gelatin | 2.0 |

The resulting product has characteristics similar to the putty of Example 53.

EXAMPLE 55

| Component 1 | Calcium Stearate | 2.0 g. |
| --- | --- | --- |
| Component 2 | Tocopheryl acetate | 1.5 g. |
| Component 3 | Pluronic ® F-38* (Molecular Wt. 4700) | 2.0 g. |

*Product 583095, Lot WP1W-515B, BASF Corp., Mt. Olive, NJ 07828-1234

Product 583095, Lot WP1W-515B, BASF, Corp. Mt. Olive, N.J. 07828-1234

The Pluronic was provided as a "Pastille" and ground to a powder before mixing. The mixture formed an excellent putty.

EXAMPLE 56

| Component 1 | Calcium Stearate | 4.0 g. |
| --- | --- | --- |
| Component 2 | Pluronic ® L-35 (Molecular Wt. 1900) | 3.0 g. |

The Pluronic® in this example was a viscous liquid and formed an excellent putty. Because this Pluronic® is water soluble, it was not necessary to add an absorption accelerant.

All of the Compositions in the following Examples 57-63 have a putty-like consistency and are easily applied to cut bone or soft tissue. Unless otherwise indicated, they are prepared by dissolving, suspending or dispersing the analgesic Component A in liquid Component 2 and Component B, if any, to form a uniform blend and then mixing that blend with solid Component 1. Percent indications are all percent by weight of the entire composition.

An evaluation of elution rates was obtained by submitting the compositions under consideration to the following: A quantity of the composition in the form of a 0.5 gm "button" having a diameter of 1 cm. is placed in 500 cc of phosphate buffer, pH 7.4, at 37° C. and slowly stirred. The surface area exposed to the buffer is about 0.785 sq. cm. One cc aliquots of the buffer solution are taken over a three day period, every 2 hours during business hours of day one, then several times on each of days two and three. Each sample is analyzed for lidocaine by HPLC-UV spectrophotometry versus a standard of lidocaine. The presence of lidocaine in the supernatant over the three day period is evidence of the release of pain-relieving amounts of the analgesic. The same procedure was followed for measurement of the elution of bupivacaine free base and hydrochloride.

In some cases, a similar amount of components was applied topically to the arm of a patient and the site of application tested with needle sticks periodically over a three day period for numbness is indication of efficasion elution of pain relieving amounts of analgesic.

EXAMPLE 57

The following compositions are prepared:

| Composition I. | Component 1. Calcium Stearate | 55% |
| | Component 2. a. Triethyl Citrate | 24% |
| | Component A. Lidocaine Free Base | 16% |
| | Component B. Tocopheryl Acetate | 5% |
| II. | Component 1. Calcium Stearate | 50% |
| | Component 2. a. Pluronic ® L-35 | 29% |
| | Component A. a. Lidocaine Free Base | 8% |
| | b. Lidocaine HCl | 8% |
| | Component B. Tocopheryl Acetate | 5% |
| III. | Component 1. Calcium Stearate | 47% |
| | Component 2. Triethyl Citrate | 37% |
| | Component A. Lidocaine HCl | 16% |
| IV. | Component 1. Calcium Stearate | 55% |
| | Component 2. a) Pluronic L-35 | 12% |
| | b) Pluronic F-68 | 12% |
| | Component A. 1. Lidocaine Free Base | 8% |
| | 2. Lidocaine HCl | 8% |
| | Component B. Tocopheryl Acetate | 5% |

Pluronic® L-35 is a liquid ethylene oxide/propylene oxide block copolymer, molecular weight about 1900, available from BASF, Mt. Olive, N.J. 07828.

Pluronic® F-68 is a solid (flake) ethylene oxide/propylene oxide block copolymer which is easily soluble in warm L-35. Pluronic® (F-68), has a molecular weight of 8,400 so that the average molecular weight of the Pluronic® Component 2 is 4,500 compared with 1,900 for L-35 alone.

To produce the Component 2 mixture with Component A, the L-35 (liquid), F-68 (solid) and the tocopheryl acetate were blended and warmed on a hot plate with swirling whereupon the solid quickly dissolved. To avoid solidification of the mixture, the liquid was not allowed to cool. While the Pluronic® mixture was still warm (not hot) and liquid, the calcium stearate was added and the mixture was stirred with a spatula in the usual way until a putty formed. This putty appeared stable in consistency at room temperature over several days and qualitatively resisted irrigation.

| V. The following Composition is prepared | | |
| --- | --- | --- |
| Component 1. | Calcium Stearate | 2.0 g |
| Component 2 | a. Tocopheryl Acetate | 1.5 g |
| Component 2 | b. Pluronic ® F-38 | 2.0 g |
| Component A | 1. Lidocaine Free Base | .65 g |
| | 2. Lidocaine HCl | .65 g |

EXAMPLE 58

| Component 1 | Calcium Stearate | 47% |
| --- | --- | --- |
| Component 2 | Pluronic ® L-35 | 28% |
| Component A. | Lidocaine HCl | 20% |
| Component B. | Tocopheryl Acetate | 5% |

EXAMPLE 59

Osteoconductive materials such as hydroxyapatite (HAP), tricalcium phosphate (TCP), A blend of HAP/TCP (40:60), a blend of HAP/TCP (20:80), having particle sizes between 0.5 and 1.5 mm. (to allow osteoconduction), are available commercially from Berkeley Advanced Biomaterial and may be added to produce any of the compositions of the invention to yield osteoconductive compositions. For example, the following:

| I. | Component 1. | Calcium Stearate | 37% |
| --- | --- | --- | --- |
| | Component 2. | Triethyl Citrate | 32% |
| | Component A. | Lidocaine | 16% |
| | Component 4. | TCP | 15% |
| II. | Component 1. | Calcium Stearate | 32.04% |
| | Component 2. | Triethyl Citrate | 24.665 |
| | Component A | 1. Lidocaine Free Base | 6.65% |
| | | 2. Lidocaine Hydrochloride | 6.65% |
| | Component 4. | Hydroxyapatite | 30.00% |
| III. | Component 1. | Calcium Stearate | 24.66% |
| | Component 2. | Pluronic ® L-35 | 32.04% |
| | Component A | 1. Lidocaine Free Base | 6.65% |
| | | 2. Lidocaine hydrochloride | 6.65% |
| | Component 4. | DBM | 30.00% |

EXAMPLE 60

| Component 1. | Calcium Stearate | 60% |
| --- | --- | --- |
| Component 2. | Triethyl Citrate | 27% |
| Component A | 1. Lidocaine Free Base | 6.5% |
| | 2. Lidocaine HCl | 6.5% |

EXAMPLE 61

| Component 1. | Calcium Stearate | 49.00% |
| --- | --- | --- |
| Component 2. | Triethyl Citrate | 37.70% |
| Component A. | 1. Lidocaine Free Base | 6.65% |
| | 2. Lidocaine Hydrochloride | 6.65% |

EXAMPLE 62

| Component 1. | Calcium Stearate | 49.0 |
| --- | --- | --- |
| Component 2. | Pluronic ® L-35 | 37.7 |
| Component A. | 1. Lidocaine Free Base | 6.65 |
| | 2. Lidocaine HCl | 6.65 |

Examples 58-62 yield products suitable as implantable pain-relieving compositions.

EXAMPLE 63

The products of the invention may be separately applied to an absorbable or non-absorbable knitted or non-woven structure or felt to provide a wound reinforcement device that will release local anesthetic to manage post-operative pain in soft tissue. The fabric component, based upon a synthetic absorbable mesh, is rapidly degraded and absorbed in situ.

For example, the product of Example 62 may be spread over a fabric mesh prior to implantation in a hernia repair operation:

| Component 1. | Calcium Stearate | 49.05 |
|---|---|---|
| Component 2. | Pluronic ® L-35 | 37.7% |
| Component A. | 1. Lidocaine Free Base | 6.65% |
|  | 2. Lidocaine HCl | 6.65% |

While the foregoing examples are given in connection with lidocaine free base and lidocaine hydrochloride, it will be appreciated that any analgesic/anesthetic free base/acid addition salt combination may be employed as well as any combination of the same or different analgesic/anesthetic in free base or acid addition salt, as appropriate. In addition, any such analgesic or combinations thereof may be included in any composition of the foregoing Examples whether or not the Example contains an analgesic.

The foregoing Examples contain illustrative specific embodiments of the present invention. Other embodiments, within the scope of the present invention, may be prepared by those skilled in the art as described in the foregoing Specification.

What is claimed is:

1. An anhydrous, body-absorbable, mechanically hemostatic putty composition comprising the following Components 1, 2, and 3:
    Component 1: a finely powdered metal salt of a fatty acid having a carboxylate anion and a metallic cation;
    Component 2: an anhydrous organic liquid comprising:
    (a) a tocopherol selected from the group consisting of tocopherol, a $C_2$-$C_{10}$ aliphatic monocarboxylic acid ester of tocopherol, a polycarboxylic acid ester of tocopherol, and mixtures thereof, and
    (b) a block copolymer of ethylene oxide and propylene oxide, and
    Component 3: a free base form of an analgesic;
    wherein Component 2 makes up 20 to 60% of the composition by weight and wherein member (a) of Component 2 makes up 5 to 44% of the composition by weight.

2. The composition of claim 1, further comprising an acid addition salt of the analgesic.

3. The composition of claim 1 wherein the carboxylate anion is selected from saturated or unsaturated carboxylic acids containing about 6 to 22 carbon atoms.

4. The composition of claim 1 wherein the carboxylate salt cation is calcium, magnesium, zinc, aluminum, or barium or mixtures thereof.

5. The composition of claim 4 wherein the carboxylate salt cation is calcium.

6. The composition of claim 4 wherein the carboxylate salt cation is aluminum.

7. The composition of claim 1 wherein the carboxylic acid supplying the carboxylate anion is an aliphatic acid selected from caprylic acid, capric acid, lauric acid, myristic acid, palmitic acid, stearic acid, arachidic acid, and intervening homologs thereof.

8. The composition of claim 7 wherein the carboxylate anion is derived from stearic acid.

9. The composition of claim 7 wherein the carboxylate anion is derived from palmitic acid.

10. The composition of claim 1, wherein the $C_2$-$C_{10}$ aliphatic monocarboxylic acid ester of tocopherol is tocopheryl acetate.

11. The composition of claim 1, wherein the analgesic is selected from the group consisting of benzocaine, bupivacaine, dibucaine, lidocaine, mepivacaine, prilocaine, procaine, chloroprocaine, etidocaine, tetracaine, and ropivacaine.

12. The composition of claim 11, wherein the analgesic is lidocaine.

13. The composition of claim 2, wherein the analgesic is selected from the group consisting of benzocaine, bupivacaine, dibucaine, lidocaine, mepivacaine, prilocaine, procaine, chloroprocaine, etidocaine, tetracaine, and ropivacaine.

14. The composition of claim 13, wherein the analgesic is lidocaine.

15. The composition of claim 2, wherein the acid addition salt of the analgesic is a hydrohalide.

16. The composition of claim 15, wherein the hydrohalide is hydrochloride or hydrobromide.

17. The composition of claim 2, wherein the analgesic is released over a period of from about 0 to 8 days.

18. The composition of claim 17, wherein the analgesic is released over a period of about 8 days.

* * * * *